(12) United States Patent
Sakuragi et al.

(10) Patent No.: US 12,038,343 B2
(45) Date of Patent: Jul. 16, 2024

(54) LOAD ESTIMATION APPARATUS, METHOD AND NON-TRANSITORY COMPUTER-READABLE STORAGE MEDIUM

(71) Applicant: KABUSHIKI KAISHA TOSHIBA, Tokyo (JP)

(72) Inventors: Rei Sakuragi, Kawasaki (JP); Kazunori Imoto, Kawasaki (JP); Tsukasa Ike, Tokyo (JP); Yasunobu Yamauchi, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 340 days.

(21) Appl. No.: 17/186,368

(22) Filed: Feb. 26, 2021

(65) Prior Publication Data

US 2022/0082462 A1   Mar. 17, 2022

(30) Foreign Application Priority Data

Sep. 14, 2020   (JP) .................................. 2020-154114

(51) Int. Cl.
 *G06F 11/30* (2006.01)
 *G01L 1/00* (2006.01)
 *G01L 5/16* (2020.01)

(52) U.S. Cl.
 CPC . *G01L 5/16* (2013.01); *G01L 1/00* (2013.01)

(58) Field of Classification Search
 CPC .................................. G01L 5/16; G01L 1/00
 See application file for complete search history.

(56) References Cited

U.S. PATENT DOCUMENTS

| | | | |
|---|---|---|---|
| 2018/0144427 A1* | 5/2018 | Ebesu | G08B 21/06 |
| 2019/0026682 A1 | 1/2019 | Ike et al. | |
| 2020/0281508 A1* | 9/2020 | Ren | A61B 5/4519 |

FOREIGN PATENT DOCUMENTS

| | | |
|---|---|---|
| JP | 2019-21051 A | 2/2019 |
| JP | 2019-103609 A | 6/2019 |
| JP | 6563076 B2 | 8/2019 |

* cited by examiner

*Primary Examiner* — Phuong Huynh
(74) *Attorney, Agent, or Firm* — Oblon, McClelland, Maier & Neustadt, L.L.P.

(57) ABSTRACT

According to one embodiment, a load estimation apparatus includes processing circuitry. The processing circuitry acquires sensor data from a measurement target, estimates an operation of a body part of the measurement target, based on the sensor data, estimates an operation load of the body part, based on information on the operation, estimates a posture of the body part, based on the sensor data, estimates a posture load of the body part, based on information on the posture, estimates a first cumulative load, based on the operation load, and estimates a second cumulative load, which requires a longer load elimination time than the first cumulative load, based on the operation load and the posture load.

11 Claims, 14 Drawing Sheets

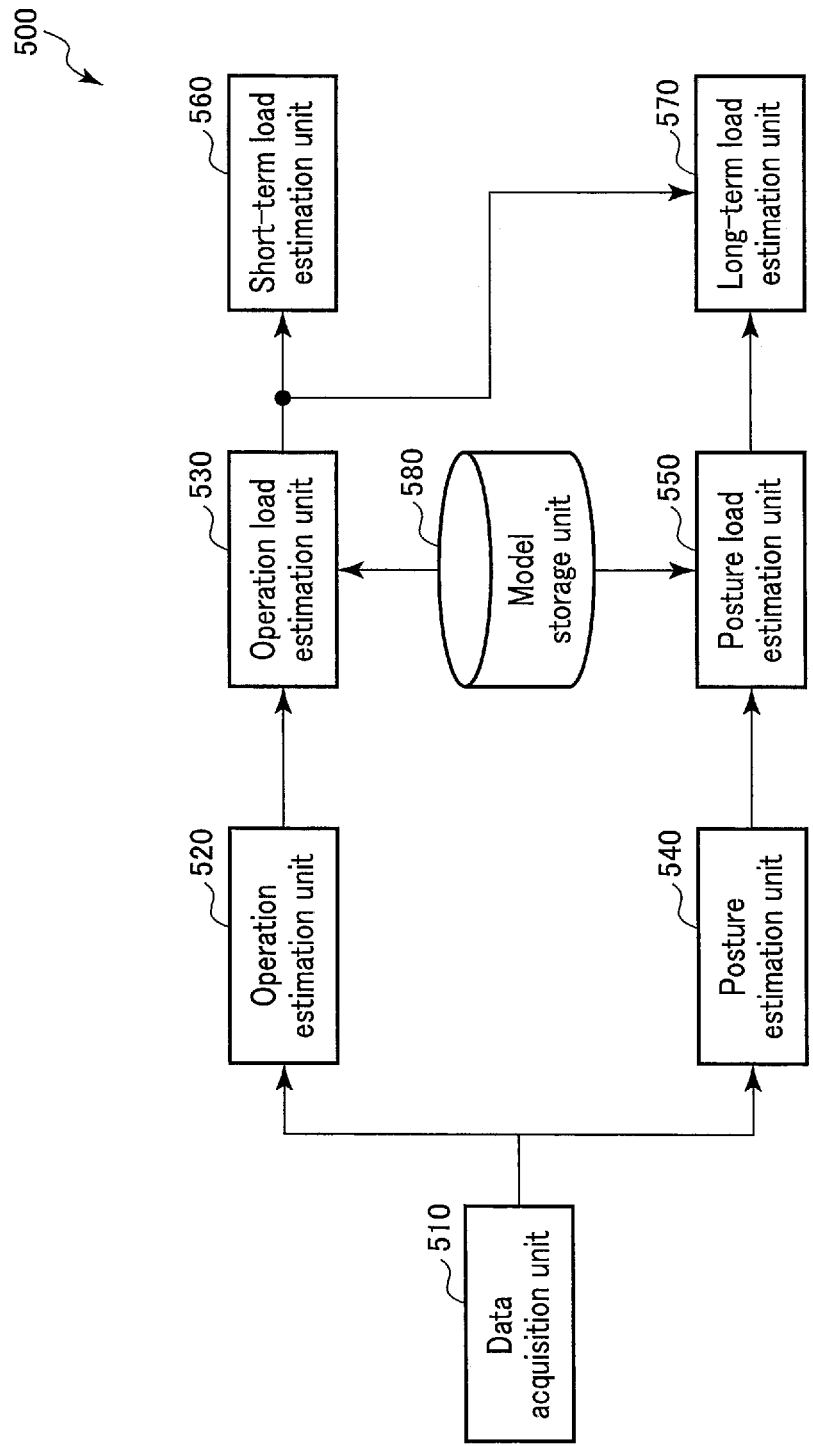
F I G. 5

600

| State of leg | | Load coefficient |
|---|---|---|
| Operation | Walking | 3 |
| | Bending and stretching | 5 |
| | Ascending | 7 |
| | Descending | 4 |
| Posture | Extension | 1 |
| | Flexion | 3 |
| | Semi-crouching | 7 |

F I G. 6

700

| State of waist | | Load coefficient |
|---|---|---|
| Operation | From flexion to extension | 5 |
| | From extension to flexion | 2 |
| Posture | Extension | 1 |
| | Flexion | 3 |
| | Seated flexion | 0 |

F I G. 7

| State of forearm | | Load coefficient |
|---|---|---|
| Operation | Bending and stretching | 2 |
| | Writing | 2 |
| Posture | Keeping in air | 2 |
| | Relaxing | 0 |

FIG. 8

| State of upper arm | | Load coefficient |
|---|---|---|
| Operation | Horizontal movement | 1 |
| | Vertical movement | 3 |
| Posture | Keeping with support | 2 |
| | Relaxing | 0 |
| | Keeping in air | 5 |

FIG. 9

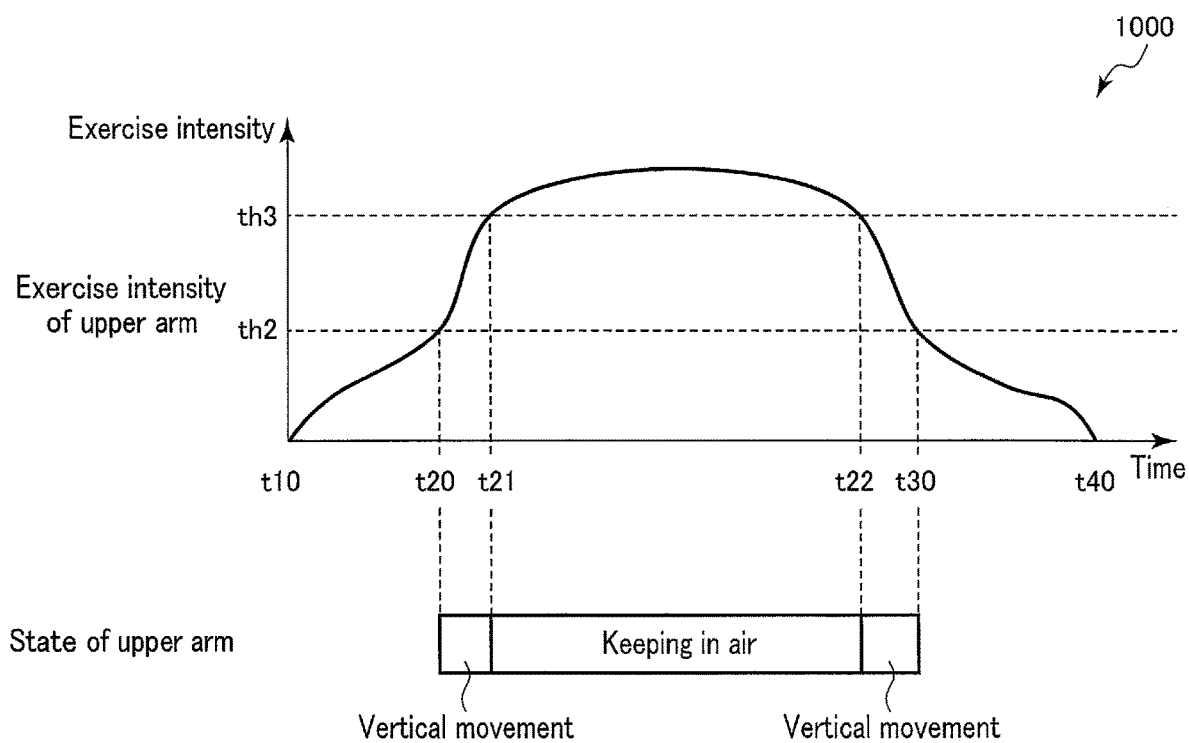
F I G. 10

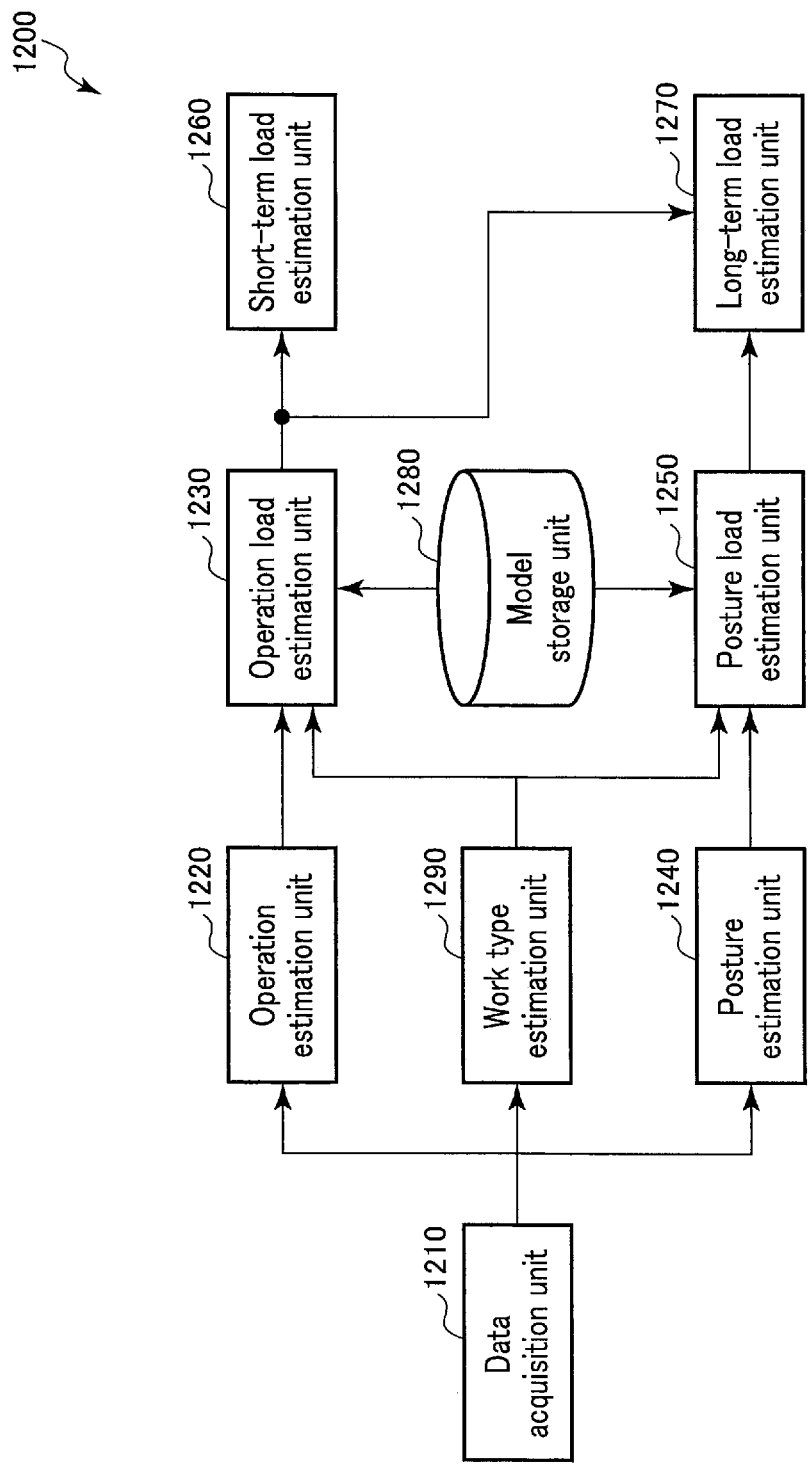
F I G. 12

| Work type | State of leg | | State of waist | | State of forearm | | State of upper arm | |
|---|---|---|---|---|---|---|---|---|
| | Operation | Posture | Operation | Posture | Operation | Posture | Operation | Posture |
| Trolley pushing | Walking | Extension | | Extension Flexion | | Keeping in air Relaxing | | Relaxing Keeping in air |
| Equipment assembly | Bending and stretching | Extension Flexion Semi-crouching | From flexion to extension From extension to flexion | Extension Flexion | Flexion | Keeping in air | Horizontal movement Vertical movement | Keeping with support |
| Brazing | | Extension | | Extension | Flexion | Keeping in air | Vertical movement | Keeping in air |
| Heavy work | Waling Bending and stretching | Extension Flexion | From flexion to extension From extension to flexion | Extension Flexion | Bending and stretching | Keeping in air | Vertical movement | Keeping in air |

F I G. 13

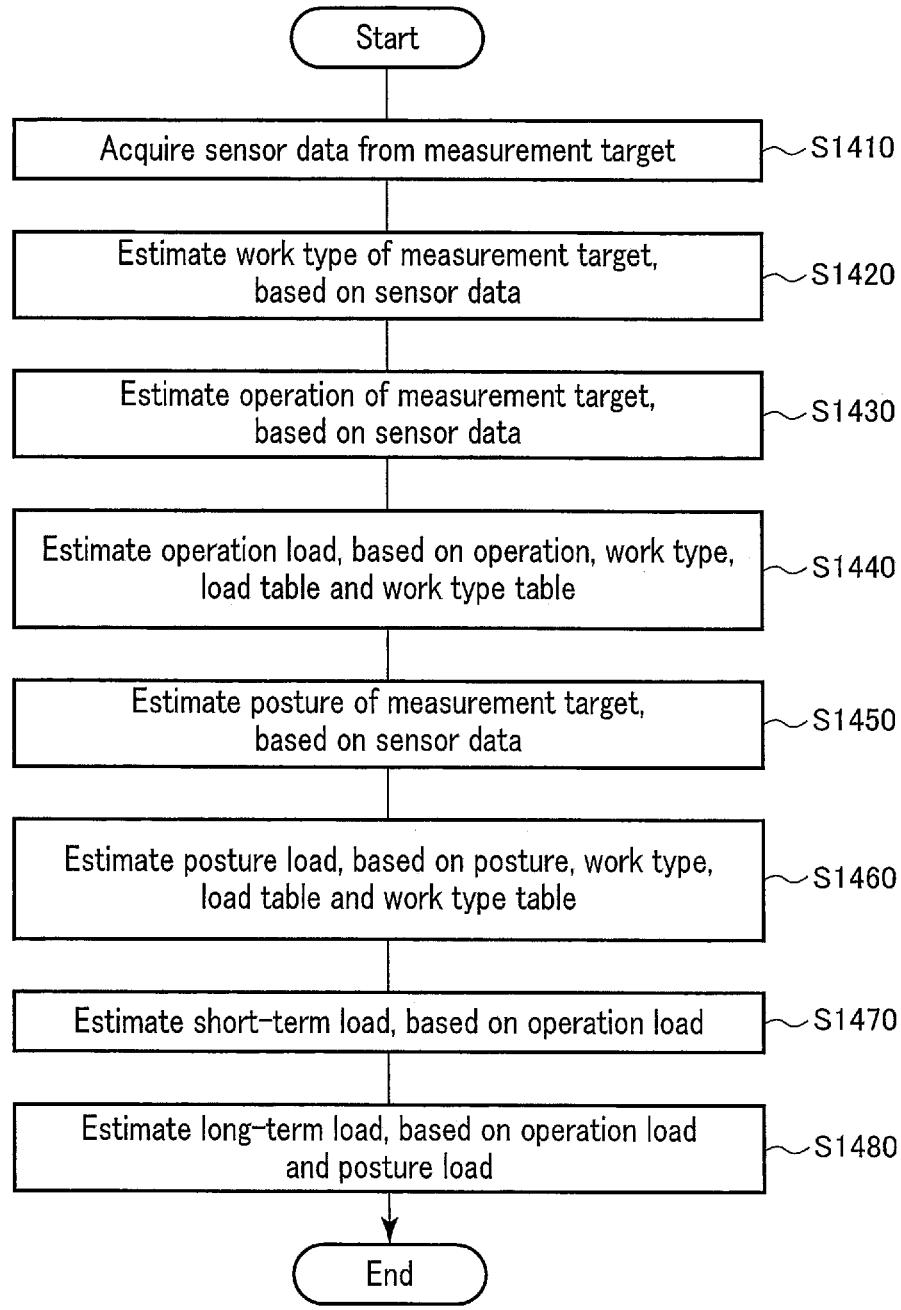
F I G. 14

| Work type | Load coefficient of leg | Load coefficient of waist | Load coefficient of forearm | Load coefficient of upper arm |
|---|---|---|---|---|
| Trolley pushing | 2 | 1 | 2 | 3 |
| Equipment assembly | 1 | 2 | 4 | 4 |
| Brazing | 4 | 3 | 3 | 3 |
| Heavy work | 5 | 5 | 4 | 4 |
F I G. 15
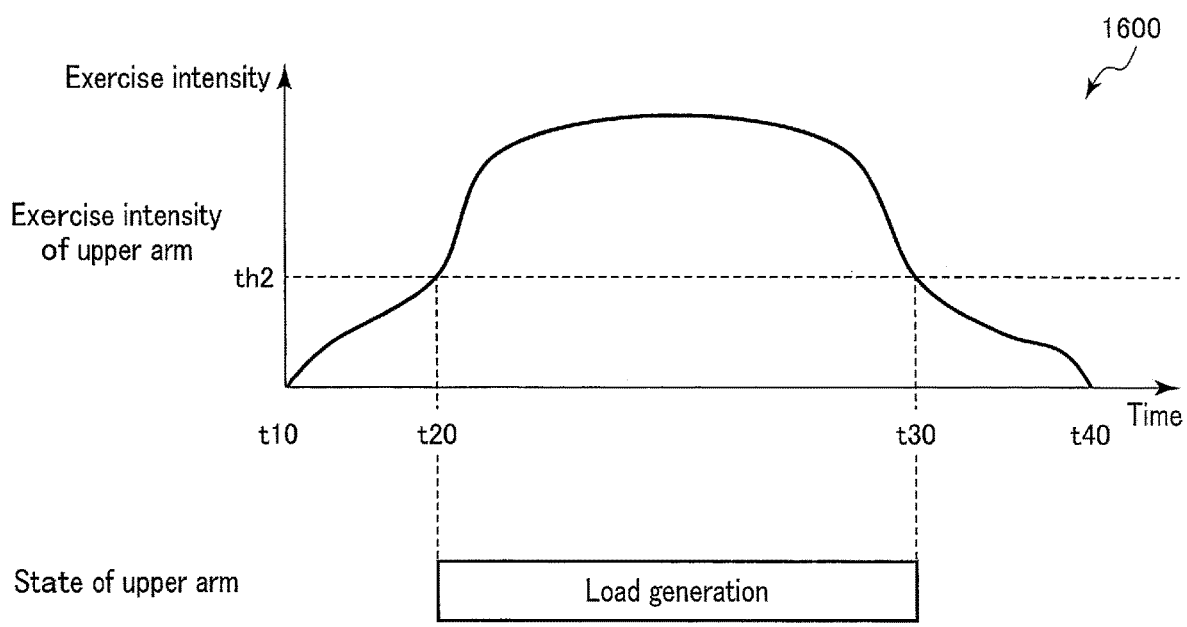
F I G. 16

| Measurement target | Long-term cumulative load value of leg | Long-term cumulative load value of waist | Long-term cumulative load value of forearm | Long-term cumulative load value of upper arm |
|---|---|---|---|---|
| Worker A | 40 | 20 | 10 | 10 |
| Worker B | 20 | 40 | 50 | 30 |
F I G. 17
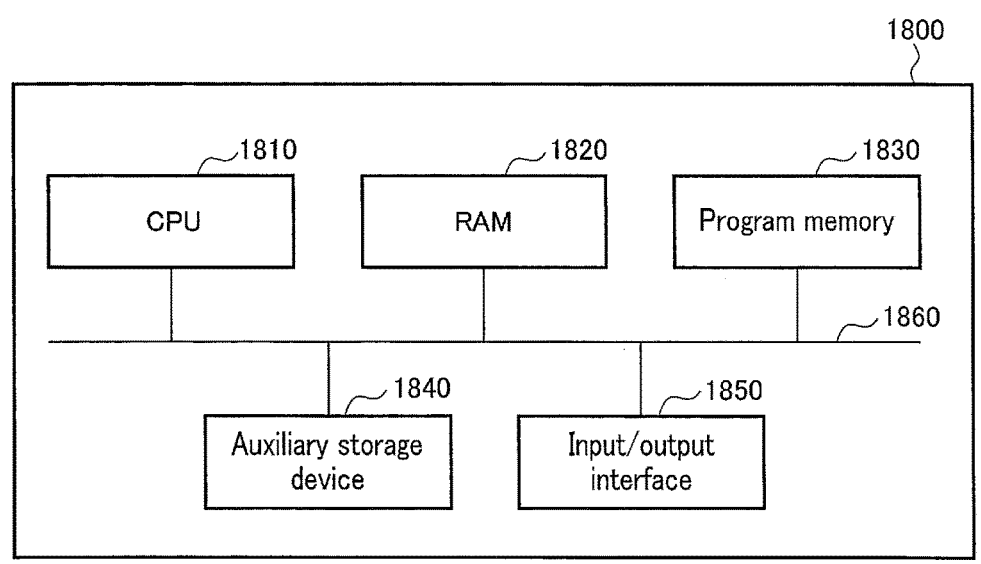
F I G. 18

LOAD ESTIMATION APPARATUS, METHOD AND NON-TRANSITORY COMPUTER-READABLE STORAGE MEDIUM

CROSS-REFERENCE TO RELATED APPLICATIONS

This application is based upon and claims the benefit of priority from Japanese Patent Application No. 2020-154114, filed Sep. 14, 2020, the entire contents of which are incorporated herein by reference.

FIELD

Embodiments described herein relate generally to a load estimation apparatus, a method and a non-transitory computer-readable storage medium.

BACKGROUND

When work time and break time of a worker are allocated at a manufacturing site, a distribution site or the like, the load of that worker has to be estimated. For example, estimating a load from a work table is known as a method of load estimation of a worker. In this method, the worker is considered to work according to a predetermined work table, and a load is estimated based on the load value associated with each work included in the work table. However, this method does not reflect the operation of the worker, so that the estimated load and the actual load may significantly differ from each other.

As another method of load estimation of a worker, a method of estimating a load using an operation sensor is known. In this method, the load is estimated from the sensor data acquired by an operation sensor mounted on the worker, and a warning is issued when the load exceeds a certain level. In this method, however, it is difficult to estimate the nature of the load, i.e., whether the load can be eliminated by taking a short rest (e.g., the rest in a break time) or whether the load requires a long rest (e.g., the work of the day has to be stopped to rest).

BRIEF DESCRIPTION OF THE DRAWINGS

FIG. 5 is a block diagram illustrating a configuration of a load estimation apparatus according to a second embodiment.

FIG. 6 is a table in which the state of a leg and a load coefficient are associated in the second embodiment.

FIG. 7 is a table in which the state of a waist and a load coefficient are associated in the second embodiment.

FIG. 8 is a table in which the state of a forearm and a load coefficient are associated in the second embodiment.

FIG. 9 is a table in which the state of an upper arm and a load coefficient are associated in the second embodiment.

FIG. 10 is a diagram illustrating how the exercise intensity of an upper arm and the state of the upper arm are related in the second embodiment.

FIG. 12 is a block diagram illustrating a configuration of a load estimation apparatus according to a third embodiment.

FIG. 13 is a table in which a work type and states of a plurality of body parts are associated in the third embodiment.

FIG. 14 is a flowchart illustrating the operation of the load estimation apparatus according to the third embodiment.

FIG. 15 is a table in which a work type and the load coefficients of a plurality of body parts are associated in an application example of the third embodiment.

FIG. 16 is a diagram illustrating how the exercise intensity of an upper arm and the state of the upper arm are related in the application example of the third embodiment.

FIG. 17 is a table in which a measurement target and long-term cumulative load values of a plurality of body parts are associated in one embodiment.

FIG. 18 is a block diagram illustrating a hardware configuration of a computer according to one embodiment.

DETAILED DESCRIPTION

In general, according to one embodiment, a load estimation apparatus includes processing circuitry. The processing circuitry acquires sensor data from a measurement target, estimates an operation of a body part of the measurement target, based on the sensor data, estimates an operation load of the body part, based on information on the operation, estimates a posture of the body part, based on the sensor data, estimates a posture load of the body part, based on information on the posture, estimates a first cumulative load, based on the operation load, and estimates a second cumulative load, which requires a longer load elimination time than the first cumulative load, based on the operation load and the posture load.

Embodiments of a load estimation apparatus will now be described in detail with reference to the accompanying drawings. The embodiments relate to a load estimation apparatus that estimates a short-term load and a long-term load by using sensor data from a measurement target. In the embodiments, the short-term load is, for example, a load that requires a short rest. The short rest is a break taken during the work of a day, such as a short rest during a break time and a lunch break. The long-term load is, for example, a load that requires a long rest. The long rest is a break taken outside the work of the day, for example, stopping the work of the day to rest, or taking the next day off to rest. In other words, the short-term load is, for example, a load that may be eliminated by taking a rest for less than a certain period of time. The long-term load is, for example, a load that may be eliminated by taking a rest for more than the certain period of time. That is, the long-term load has a property that the period required for load elimination is longer than that of the short-term load.

First Embodiment

Figure 1:
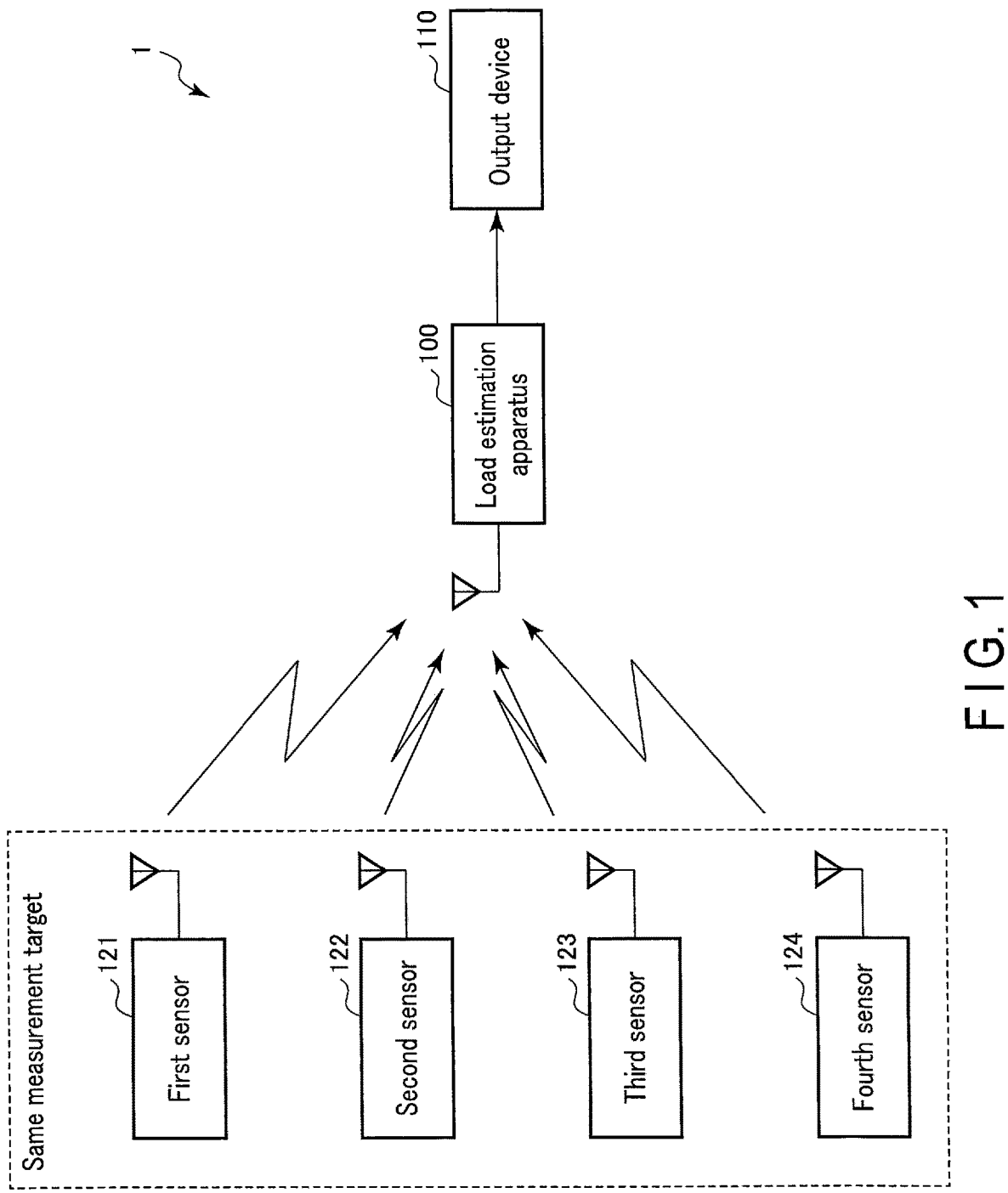
FIG. 1 is a block diagram illustrating a configuration of a load estimation system including a load estimation apparatus according to a first embodiment.

FIG. 1 is a block diagram illustrating a configuration of a load estimation system including a load estimation apparatus according to a first embodiment. The load estimation system 1 shown in FIG. 1 includes a load estimation apparatus 100, an output device 110, and one or more sensors. In FIG. 1, a first sensor 121, a second sensor 122, a third sensor 123 and a fourth sensor 124 are illustrated as the one or more sensors. The one or more sensors acquire one or more sensor data from the same measurement target.

The load estimation apparatus 100 estimates a short-term load and a long-term load, based on the one or more sensor data. The output device 110 displays display data that is based on the short-term load and the long-term load. The load estimation system 1 may include a sensor that acquires sensor data from another measurement target. The measurement target is, for example, a worker who works at a work site such as a factory.

The output device 110 is, for example, a monitor. The output device 110 receives display data from the load estimation apparatus 100. The output device 110 displays the display data. The output device 110 is not limited to the monitor as long as the display data can be displayed. For example, the output device 110 may be a projector or a printer. The output device 110 may include a speaker.

The one or more sensors are built into, for example, a wearable device worn on a plurality of body parts of a measurement target. In the description below, the wearable device and the sensor will be used refer to the same element. The plurality of body parts are, for example, a wrist, an upper arm, an ankle, a thigh, a hip, a back and a head. Each sensor of the one or more sensors acquires, as sensor data, at least one measurement data, such as acceleration data, angular velocity data, geomagnetic data, pressure data, temperature/humidity data, myoelectric potential data and pulse rate data. Preferably, each sensor acquires at least acceleration data and angular velocity data as sensor data. The measurement data may include a plurality of channels. For example, where the measurement data is acceleration data, the sensor data includes measurement data for three channels corresponding to the directions of acceleration. Where the measurement data is angular velocity data, the sensor data includes measurement data for three channels corresponding to the directions of angular velocity. In the present embodiment, reference will be made to the case where the first sensor 121, the second sensor 122, the third sensor 123 and the fourth sensor 124 are used as the one or more sensors.

The first sensor 121 is attached to, for example, an ankle of the measurement target. The first sensor 121 measures the state of the leg of the measurement target, as sensor data. The first sensor 121 outputs the measured sensor data to the load estimation apparatus 100.

The second sensor 122 is attached to, for example, a waist of the measurement target. The second sensor 122 measures the state of the waist of the measurement target, as sensor data. The second sensor 122 outputs the measured sensor data to the load estimation apparatus 100.

The third sensor 123 is attached to, for example, a wrist of the measurement target. The third sensor 123 measures the state of the wrist (forearm) of the measurement target, as sensor data. The third sensor 123 outputs the measured sensor data to the load estimation apparatus 100.

The fourth sensor 124 is attached to, for example, an upper arm of the measurement target. The fourth sensor 124 measures the state of the upper arm of the measurement target, as sensor data. The fourth sensor 124 outputs the measured sensor data to the load estimation apparatus 100.

Figure 2:
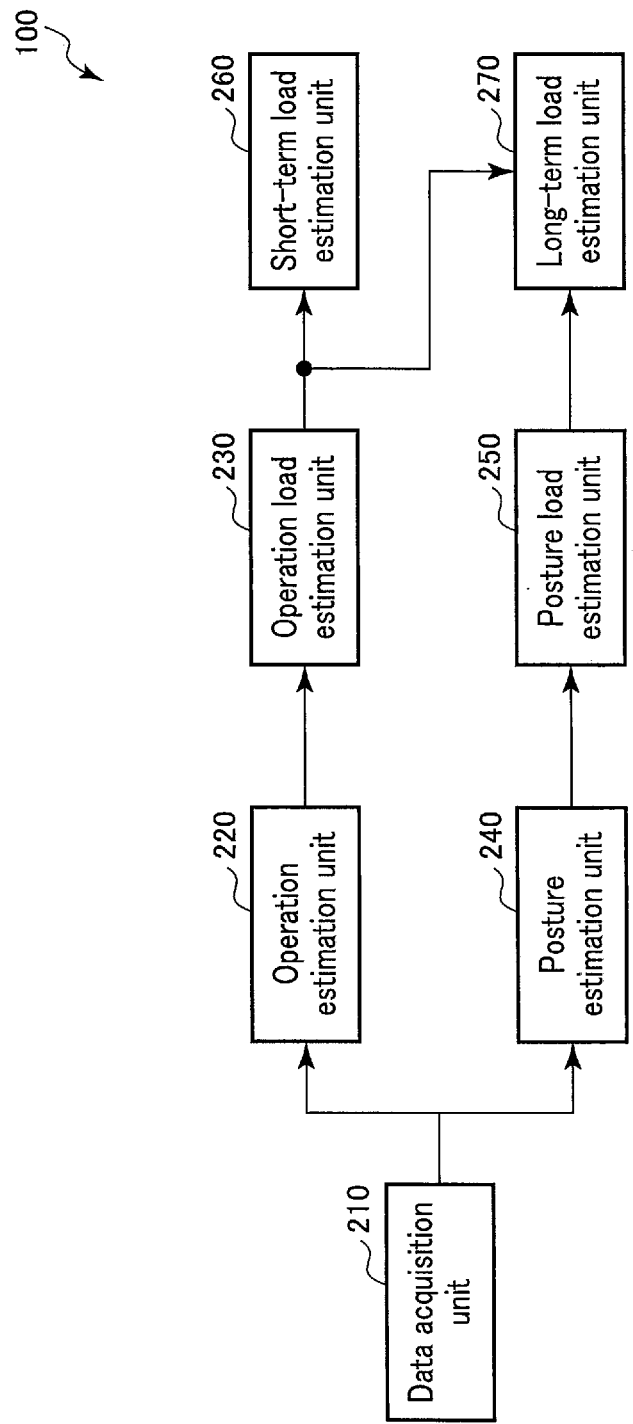
FIG. 2 is a block diagram illustrating a configuration of the load estimation apparatus according to the first embodiment.

FIG. 2 is a block diagram illustrating a configuration of the load estimation apparatus according to the first embodiment. The load estimation apparatus 100 shown in FIG. 2 includes a data acquisition unit 210 (acquisition unit), an operation estimation unit 220, an operation load estimation unit 230, a posture estimation unit 240, a posture load estimation unit 250, a short-term load estimation unit 260 (first cumulative load estimation unit) and a long-term load estimation unit 270 (second cumulative load estimation unit). The operation estimation unit 220 and the posture estimation unit 240 may be integrated as one estimation unit. In other words, the operation estimation unit 220 may perform each process of the posture estimation unit 240, or the posture estimation unit 240 may perform each process of the operation estimation unit 220.

The data acquisition unit 210 acquires sensor data from each of the first sensor 121, the second sensor 122, the third sensor 123 and the fourth sensor 124. In the description below, where each sensor data need not be distinguished, each sensor data will be referred to simply as sensor data. The data acquisition unit 210 outputs the acquired sensor data to the operation estimation unit 220 and the posture estimation unit 240. The data acquisition unit 210 may store the acquired sensor data in a storage unit (not shown) or transmit it to an external server.

The operation estimation unit 220 receives sensor data from the data acquisition unit 210. The operation estimation unit 220 estimates an operation of a body part of the measurement target, based on the sensor data. The operation estimation unit 220 outputs information on the estimated operation (operation information) to the operation load estimation unit 230. The operation estimation unit 220 may estimate an operation of a specific body part by using sensor data from one or more sensors attached to one or more body parts including the specific body part. Alternatively, the operation estimation unit 220 may estimate an operation of the specific body part and an operation of one or more other body parts. Further, the operation estimation unit 220 may estimate an operation of the whole body of the measurement target.

Specifically, the operation estimation unit 220 estimates the momentum of the body part of the measurement target, based on the pattern of the sensor data. More specifically, the operation estimation unit 220 calculates the product of the amount of operation of the body part and the time for which the body part moves, by using, for example, a pattern of the difference between the sensor pattern acquired at rest and the sensor pattern acquired at work, and may calculate a momentum by using the double integration of acceleration measurement. In addition, the operation estimation unit 220 may calculate the momentum by executing one or more commonly known algorithms. The operation estimation unit 220 may calculate the exercise intensity from the momentum.

The operation estimation unit 220 may estimate the type of operation of the body part. In this case, the operation estimation unit 220 may estimate the operation type, by using a learned machine learning model trained to output a type of operation of the body part in response to input of sensor data. Further, the operation estimation unit 220 may estimate at least one of whether the measurement target is at work and whether it is at rest, from the pattern of the sensor data.

The operation load estimation unit 230 receives operation information from the operation estimation unit 220. The operation load estimation unit 230 estimates an operation load, based on the operation information. The operation load estimation unit 230 outputs information on the estimated operation load (operation load information) to the short-term load estimation unit 260 and the long-term load estimation unit 270.

Specifically, where the operation information includes a momentum, the operation load estimation unit 230 estimates an operation load, for example, by executing one or more generally known algorithms for the calculated momentum.

The posture estimation unit 240 receives sensor data from the data acquisition unit 210. The posture estimation unit 240 estimates a posture of the measurement target, based on the sensor data. The posture estimation unit 240 outputs information on the estimated posture (posture information) to the posture load estimation unit 250. The posture estimation unit 240 may estimate a posture of a specific body part by using sensor data from one or more sensors attached to one or more body parts including the specific body part. Alternatively, the posture estimation unit 240 may estimate the posture of the specific body part and the posture of one or more other body parts. Further, the posture estimation unit 240 may estimate a posture of the whole body of the measurement target.

Specifically, the posture estimation unit 240 estimates a posture type of the body part of the measurement target, based on the pattern of sensor data. More specifically, the posture estimation unit 240 estimates the posture type, for example, by feature amount matching using a table in which the feature amount of the sensor pattern and the posture type are associated with each other. In addition, the posture estimation unit 240 may calculate the posture type by executing one or more generally known algorithms. Further, the posture estimation unit 240 may estimate the posture type by using a learned machine learning model trained to output a posture type in response to input of sensor data.

The posture estimation unit 240 may estimate at least one of whether the measurement target is at work or whether it is at rest from the pattern of the sensor data.

The posture load estimation unit 250 receives posture information from the posture estimation unit 240. The posture load estimation unit 250 estimates a posture load, based on the posture information. The posture load estimation unit 250 outputs information on the estimated posture load (posture load information) to the long-term load estimation unit 270.

Specifically, the posture load estimation unit 250 estimates a posture load by executing one or more generally known algorithms for the posture information.

The short-term load estimation unit 260 receives operation load information from the operation load estimation unit 230. The short-term load estimation unit 260 estimates a short-term load (first cumulative load), based on the operation load information. Specifically, the short-term load estimation unit 260 estimates a short-term load by accumulating the same operation loads performed within a predetermined time. The short-term load estimation unit 260 may reduce the addition rate of cumulative loads in accordance with an increase in the number of times the same operation load is performed within the predetermined time.

Where the operation load is expressed as a set of operation and load value, the short-term load estimation unit 260 may accumulate the short-term load by accumulating the load values for the same operation performed within the predetermined time.

The long-term load estimation unit 270 receives operation load information from the operation load estimation unit 230 and posture load information from the posture load estimation unit 250. The long-term load estimation unit 270 estimates a long-term load (second cumulative load), based on the operation load information and the posture load information. Specifically, the long-term load estimation unit 270 estimates the long-term load, based on the number of times the same operation load is performed during a predetermined time and the duration of the same posture load. The long-term load estimation unit 270 may calculate an estimated time required for load elimination, based on the estimated long-term load.

Figure 3:
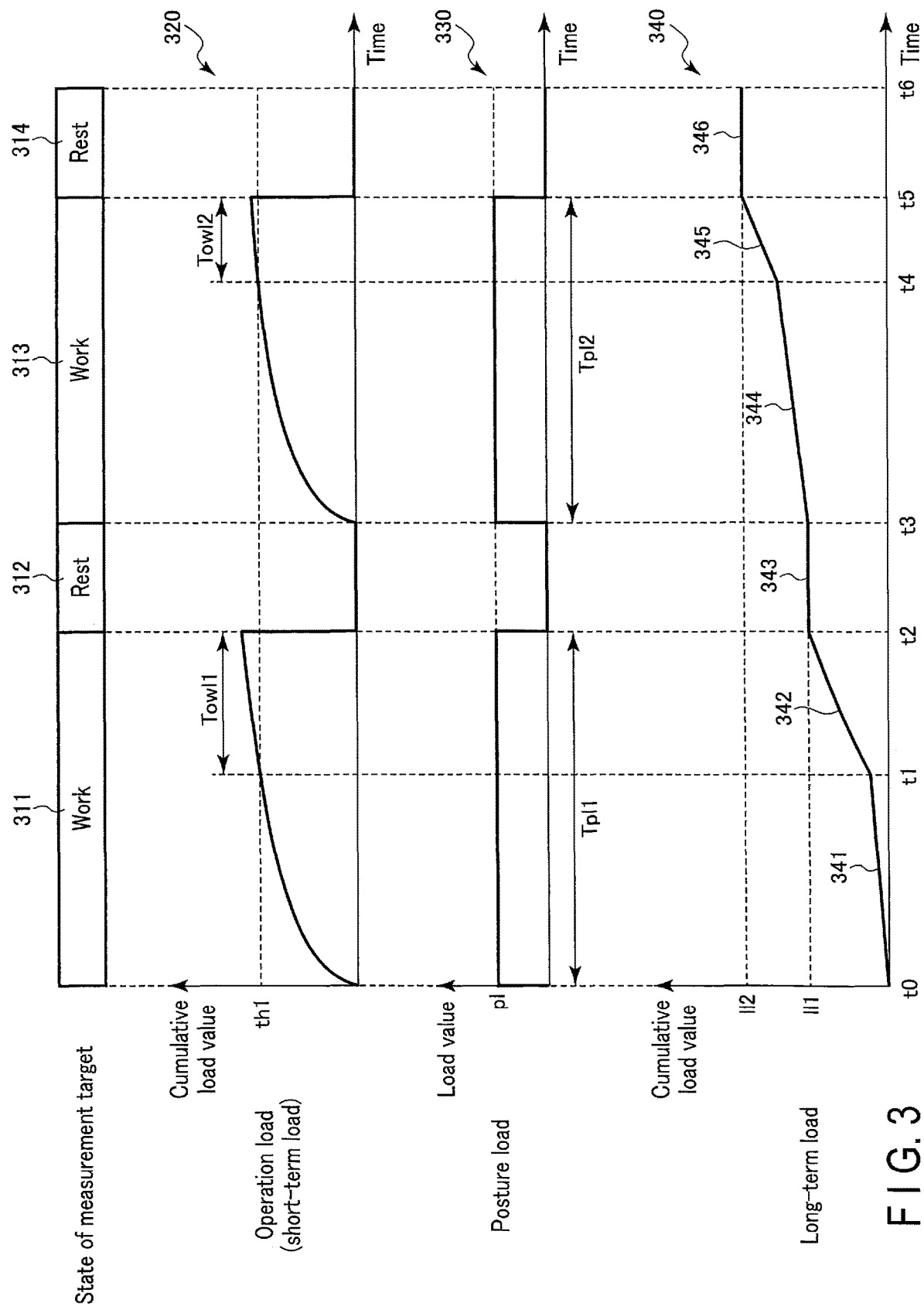
FIG. 3 is a diagram illustrating how the state of a measurement target, an operation load, a posture load and a long-term load are related in the first embodiment.

FIG. 3 is a diagram illustrating how the state of a measurement target, an operation load, a posture load and a long-term load are related in the first embodiment. In FIG. 3, four states 311 to 314 are shown in chronological order as the states of the measurement target. Specifically, the state 311 indicates that a work is performed from time t0 to time t2. The state 312 indicates that the measurement target is at rest from time t2 to time t3. The state 313 indicates that a work is performed from time t3 to time t5. The state 314 indicates that the measurement target was at rest from time t5 to time t6.

FIG. 3 shows a graph 320, a graph 330 and a graph 340 in correspondence to the period from time t0 to time t6. The graph 320 corresponds to an operation load (short-term load), the graph 330 corresponds to a posture load, and the graph 340 corresponds to a long-term load. It is assumed that the graph 320, graph 330 and graph 340 shown in FIG. 3 are related to a specific operation or a specific posture. The operation and posture may be inferred, for example, from the waveform of sensor data. In the description below, it is assumed that a specific operation and a specific posture of the measurement target are estimated.

When the measurement target starts work at time t0, the operation load estimation unit 230 estimates an operation load of the measurement target.

Further, the short-term load estimation unit 260 accumulates load values included in the estimated operation load information with time. As a result, the waveform of the graph 320 shows a cumulative value of the load value (cumulative load value) that increases non-linearly from time t0 to time t2.

At time t0, the posture load estimation unit 250 estimates a posture load of the measurement target. For the convenience of description, it is assumed that the measurement target continues to maintain a specific posture during work. It is also assumed that the posture load information includes a load value corresponding to the specific posture. Thus, in the waveform of the graph 330, a load value p1 corresponding to the specific posture is shown as being constant from time t0 to time t2.

At time t0, the long-term load estimation unit 270 accumulates load values that can be long-term loads with time, based on the operation load information and the posture load information. For example, the long-term load estimation unit 270 accumulates load values of the posture load with time from in the period from time t0 to time t2, which period corresponds to a time length Tp11 when a posture load is continuously generated. Further, the long-term load estimation unit 270 further accumulates the load values of the short-term load in the period from time t1 to time t2 during which the cumulative load value of the short-term load exceeds a threshold value th1. As a result, the waveform of the graph 340 shows a cumulative value of the load value (cumulative load value) that increases substantially linearly from time t0 to time t1 and from time t1 to time t2. Further, in the waveform of the graph 340, the slope of the section 342 corresponding to the period from time t1 to time t2 is shown as being larger than the slope of the section 341 corresponding to the period from time t0 to time t1. This means that after time t1, the operation load is included in the long-term load.

Next, at time t2, the short-term load estimation unit 260 ends the accumulation of load values upon detection of the rest state of the measurement target, and sets the cumulative load value to the initial value (e.g., zero). In the rest state, the load estimation is not performed. Therefore, the waveform of the graph 320 shows a cumulative load value indicative of zero from time t2 to time t3.

At time t2, the posture load estimation unit 250 estimates that the measurement target is in the rest state, and does not estimate the load value or sets the load value to zero. As a result, the waveform of the graph 330 shows a load value indicative of zero from time t2 to time t3.

At time t2, there is no operation load or posture load that is included in the long-term load, so that the estimation unit 270 maintains the same cumulative load value. Thus, in the waveform of the graph 340, the cumulative load value accumulated during the section 341 and the section 342 is shown as the cumulative load value 111 in the section 343 from time t2 to time t3.

At time t3, when the measurement target starts work again, the operation load estimation unit 230 estimates an operation load of the measurement target. Further, the short-term load estimation unit 260 accumulates load values included in the estimated operation load information with time. Thus, the waveform of the graph 320 shows a cumulative load value that increases non-linearly from time t3 to time t5.

At time t3, the posture load estimation unit 250 estimates a posture load of the measurement target. It is assumed here that the measurement target is performing the same work as in the state 311. Thus, in the waveform of the graph 330, the load value pl is shown as being constant from time t3 to time t5.

At time t3, the long-term load estimation unit 270 accumulates load values that can be long-term loads with time, based on the operation load information and the posture load information. For example, the long-term load estimation unit 270 accumulates load values of the posture load with time in the period from time t3 to time t5, which period corresponds to a time length Tp12 when a posture load is continuously generated. Further, the long-term load estimation unit 270 further accumulates the load values of the short-term load in the period from time t4 to time t5 in which the cumulative load value of the short-term load exceeds the threshold value th1. As a result, the waveform of the graph 340 shows a cumulative load value that increases substantially linearly from time t3 to time t4 and from time t4 to time t5. Further, in the waveform of the graph 340, the slope of the section 345 corresponding to the period from time t4 to time t5 is shown as being larger than the slope of the section 344 corresponding to the period from time t3 to time t4. This means that after time t4, the operation load is included in the long-term load.

Next, at time t5, the short-term load estimation unit 260 ends the accumulation of load values upon detection of the rest state of the measurement target, and sets the cumulative load value to zero. Therefore, the waveform of the graph 320 shows a cumulative load value indicative of zero from time t5 to time t6.

At time t5, the posture load estimation unit 250 estimates that the measurement target is in the rest state, and does not estimate the load value or sets the load value to zero. As a result, the waveform of the graph 330 shows a load value indicative of zero from time t5 to time t6.

At time t5, there is no operation load or posture load that is included in the long-term load, so that the estimation unit 270 maintains the same cumulative load value. Thus, the waveform of the graph 340 shows that the cumulative load value accumulated during the section 344 and the section 345 is the cumulative load value 112 in the section 346 from time t5 to time t6, with the cumulative load value 111 as a base.

The load estimation apparatus 100 may include a memory and a processor (neither is shown). The memory stores, for example, various programs related to the operation of the load estimation apparatus 100 (e.g., a load estimation program for estimating a load of a worker). By executing the various programs stored in the memory, the functions of the data acquisition unit 210, the operation estimation unit 220, the operation load estimation unit 230, the posture estimation unit 240, the posture load estimation unit 250, the short-term load estimation unit 260 and the long-term load estimation unit 270 are realized.

The configurations of the load estimation system 1 and load estimation apparatus 100 according to the first embodiment have been described above. Next, the operation of the load estimation apparatus 100 will be described with reference to the flowchart of FIG. 4.

Figure 4:
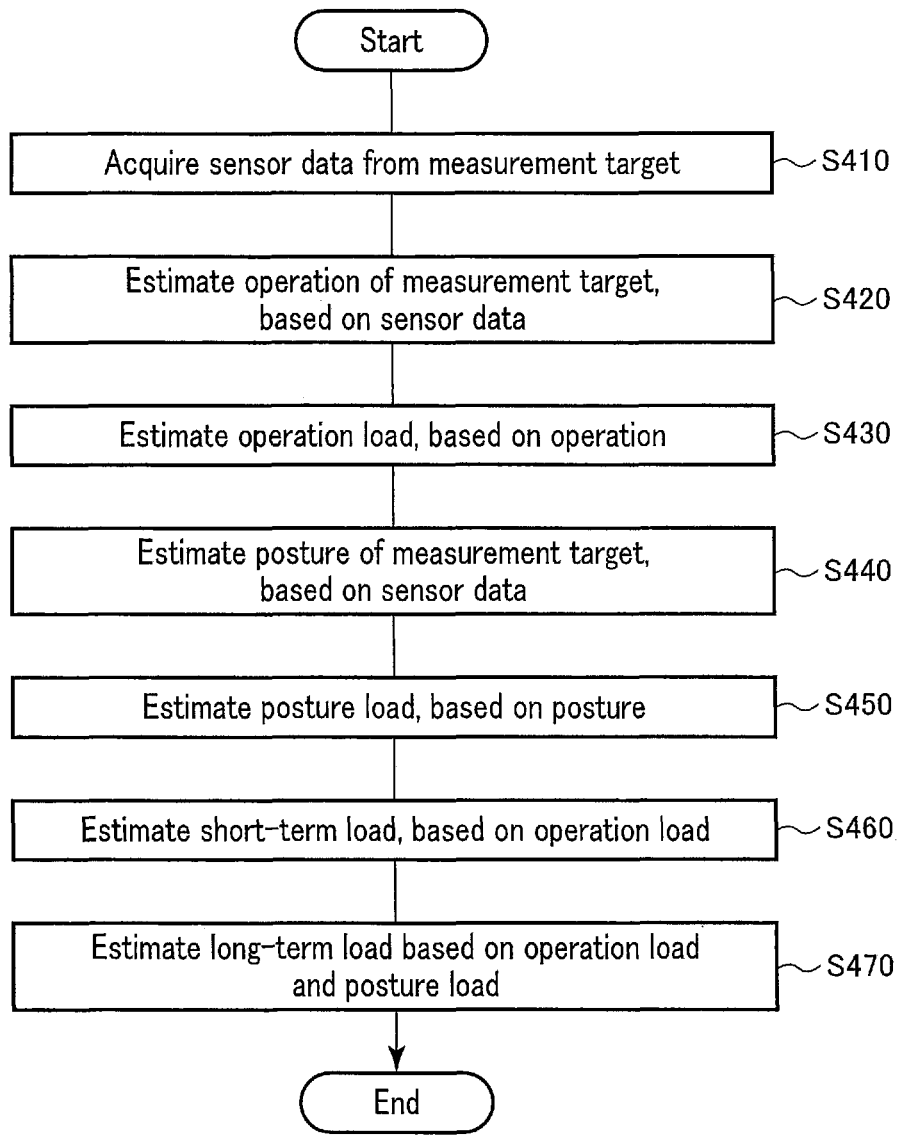
FIG. 4 is a flowchart illustrating an operation of the load estimation apparatus according to the first embodiment.

FIG. 4 is a flowchart illustrating the operation of the load estimation apparatus according to the first embodiment. The process of the flowchart of FIG. 4 starts when the load estimation program is executed by the user.

(Step S410)
When the load estimation program is executed, the data acquisition unit 210 acquires sensor data from the measurement target.

(Step S420)
After the sensor data is acquired, the operation estimation unit 220 estimates an operation of the measurement target, based on the acquired sensor data.

(Step S430)
After the operation is estimated, the operation load estimation unit 230 estimates an operation load, based on the estimated operation.

(Step S440)
After the operation load is estimated, the posture estimation unit 240 estimates a posture of the measurement target, based on the sensor data.

(Step S450)
After the posture is estimated, the posture load estimation unit 250 estimates a posture load based on the estimated posture.

The processing of step S440 and step S450 may be performed after the processing of step S410. Further, the processing of step S440 and S450 may be performed together with the processing of steps S420 and S430.

(Step S460)
After the posture load is estimated, the short-term load estimation unit 260 estimates a short-term load, based on the estimated operation load.

(Step S470)
After the short-term load is estimated, the long-term load estimation unit 270 estimates a long-term load, based on the estimated operation load and the estimated posture load. After the processing of step S470, the load estimation program is terminated. The processing of step S470 may be performed together with the processing of step S460.

Where sensor data is acquired in real time, the process flow returns to step S410 after the processing of step S470, and the subsequent processes are repeated. The load estimation program may be ended in response to an instruction by the user.

As described above, the load estimation apparatus according to the first embodiment acquires sensor data from the measurement target, estimates an operation of a body part of the measurement target, based on the sensor data, estimates an operation load of the body part, based on operation information, estimates a posture of the body part, based on the sensor data, estimates a posture load of the body part, based on information on the posture, estimates a first cumulative load, based on the operation load, and estimates a second cumulative load, which requires a longer load elimination time than the first cumulative load, based on the operation load and posture load.

Therefore, the load estimation apparatus according to the first embodiment can perform load estimation in consideration of the nature of a load. Further, the load estimation apparatus according to the first embodiment enables creation of a work plan that efficiently enhances the productivity of a worker.

Second Embodiment

In connection with the first embodiment, a description was given of the basic configuration and operation of the load estimation apparatus. In connection with the second embodiment, a description will be given of the case where a load estimation apparatus performs operation load estimation and posture load estimation by using a load coefficient corresponding to the state of a body part.

FIG. 5 is a block diagram illustrating the configuration of the load estimation apparatus according to the second embodiment. The load estimation apparatus 500 shown in FIG. 5 includes a data acquisition unit 510, an operation estimation unit 520, an operation load estimation unit 530, a posture estimation unit 540, a posture load estimation unit 550, a short-term load estimation unit 560 (first cumulative load estimation unit), along-term load estimation unit 570 (second cumulative load estimation unit) and a model storage unit 580. The configurations of the data acquisition unit 510, operation estimation unit 520, posture estimation unit 540, short-term load estimation unit 560 and long-term load estimation unit 570 are similar to those of the data acquisition unit 210, operation estimation unit 220, posture estimation unit 240, short-term load estimation unit 260 and the long-term load estimation unit 270, and a description of the configurations will be omitted.

The model storage unit 580 stores a load table (first table) in which states of body parts and load coefficients are associated with each other. The body parts are, for example, a leg, a hip, an upper arm and a forearm. The states of body parts are, for example, an operation and a posture. The load coefficients are classified according to the degree of load, for example. Each load coefficient is determined based on, for example, at least either of the ratio of the weight of a body part to the weight of the whole body and the relationship between the weight of the body part and the muscle mass of the body part. The model storage unit 580 outputs a load table to the operation load estimation unit 530 and the posture load estimation unit 550.

FIG. 6 is a table in which the state of a leg and a load coefficient are associated in the second embodiment. In the table 600 (load table) of FIG. 6, the state of the leg is either an operation or a posture. The operations that are states of the leg (operations of the leg) are classified into, for example, "walking", "bending and stretching", "ascending" and "descending." Load coefficients "3", "5", "7" and "4" are associated with of the classified operations of the leg, respectively. The postures that are states of the leg (postures of the leg) are classified into, for example, "extension", "flexion" and "semi-crouching." Load coefficients "1", "3", and "7" are associated with the classified postures of the leg, respectively.

FIG. 7 is a table in which the state of a leg and a load coefficient are associated in the second embodiment. In the table 700 (load table) of FIG. 7, the state of a waist is either an operation or a posture. The operations that are states of the waist (operations of the waist) are classified into, for example, "flexion to extension" and "extension to flexion." Load coefficients "5" and "2" are associated with the classified operations of the waist, respectively. The postures that are states of the waist (postures of the waist) are classified into, for example, "extension", "flexion" and "seated flexion." Load coefficients "1", "3", and "0" are associated with the classified postures of the waist, respectively.

FIG. 8 is a table in which the state of a forearm and a load coefficient are associated in the second embodiment. In the table 800 (load table) of FIG. 8, the state of the forearm is either an operation or a posture. The operations that are states of the forearm (operations of the forearm) are classified into, for example, "flexion" and "writing." Load coefficients "2" and "2" are associated with the classified operations of the forearm, respectively. The postures that are states of the forearm (postures of the forearm) are classified into, for example, "keeping in air" and "relaxing." Load coefficients "2" and "0" are associated with the classified postures of the forearm, respectively.

FIG. 9 is a table in which the state of the upper arm and the load coefficient are associated in the second embodiment. In the table 900 (load table) of FIG. 9, the state of the upper arm is either an operation or a posture. The operations that are states of the upper arm (operations of the upper arm) are classified into, for example, "horizontal movement" and "vertical movement." Load coefficients "1" and "3" are associated with the classified operations of the upper arm, respectively. The postures that are states of the upper arm (postures of the upper arm) are classified into, for example, "keeping with support", "relaxing" and "keeping in air." Load coefficients "2", "0", and "5" are associated with the classified postures of the upper arm, respectively.

The operation load estimation unit 530 receives operation information from the operation estimation unit 520 and reads a load table from the model storage unit 580. The operation load estimation unit 530 estimates an operation load, based on the operation information and the load table. The operation load estimation unit 530 outputs information on the estimated operation load (operation load information) to the short-term load estimation unit 560 and the long-term load estimation unit 570.

Specifically, where the operation information includes an operation of a body part and exercise intensity in the operation of the body part, the operation load estimation unit 530 estimates a load value (operation load) by executing a predetermined operation (e.g., multiplication) using, for example, the coefficients corresponding to the exercise intensity in the operation of the body part and the operation of the body part.

The posture load estimation unit 550 receives posture information from the posture estimation unit 540 and reads a load table from the model storage unit 580. The posture load estimation unit 550 estimates a posture load, based on the posture information and the load table. The posture load estimation unit 550 outputs information on the estimated posture load (posture load information) to the long-term load estimation unit 570.

Specifically, where the posture information includes a posture of a body part and duration of the posture of the body part, the posture load estimation unit 550 estimates a load value (posture load) by executing a predetermined operation (e.g., multiplication) using, for example, the coefficients corresponding to the duration of the posture of the body part and the posture of the body part.

FIG. 10 is a diagram illustrating how the exercise intensity of an upper arm and the state of the upper arm are related in the second embodiment. FIG. 10 shows a graph 1000 that expresses the exercise intensity of the upper arm in chronological order. For example, where the exercise intensity of the upper arm exceeds a first threshold value (threshold value th2), the operation estimation unit 520 estimates that the upper arm is vertically moving. Where the exercise intensity of the upper arm exceeds a second threshold value (threshold value th3) larger than the threshold value th2, the operation estimation unit 520 estimates that the upper arm is in the posture of being kept in the air.

Specifically, in the graph 1000, the exercise intensity of the upper arm increases from time t10, and at time t20, the exercise intensity of the upper arm exceeds the threshold value th2. Further, in the graph 1000, the exercise intensity continues to increase, and at time t21, the exercise intensity of the upper arm exceeds the threshold value th3. The state of exceeding the threshold value th3 is maintained until time t22. In the graph 1000, the exercise intensity of the upper arm falls below the threshold value th3 at time t22, falls below the threshold value th2 at time t30, and becomes the initial value (zero) at time t40.

The operation estimation unit 520 estimates that the period from time t20 to time t21 corresponds to a vertical movement operation, that the period from time t21 to time t22 corresponds to a posture of being kept in the air, and that the period from time t22 to time t30 corresponds to a vertical movement operation. The operation estimation unit 520 does not have to estimate the posture of being kept in the air. For example, the operation estimation unit 520 may estimate from the pattern of the sensor data that the period from time t21 to time t22 has nothing to do with the operation of the upper arm. In this case, the posture estimation unit 540 estimates from the pattern of the sensor data that the period from time t21 to time t22 is a period in which the upper arm is kept in the air (the posture of being kept in the air).

The configuration of the load estimation apparatus 500 according to the second embodiment has been described above. Next, the operation of the load estimation apparatus 500 will be described with reference to the flowchart of FIG. 11.

Figure 11:
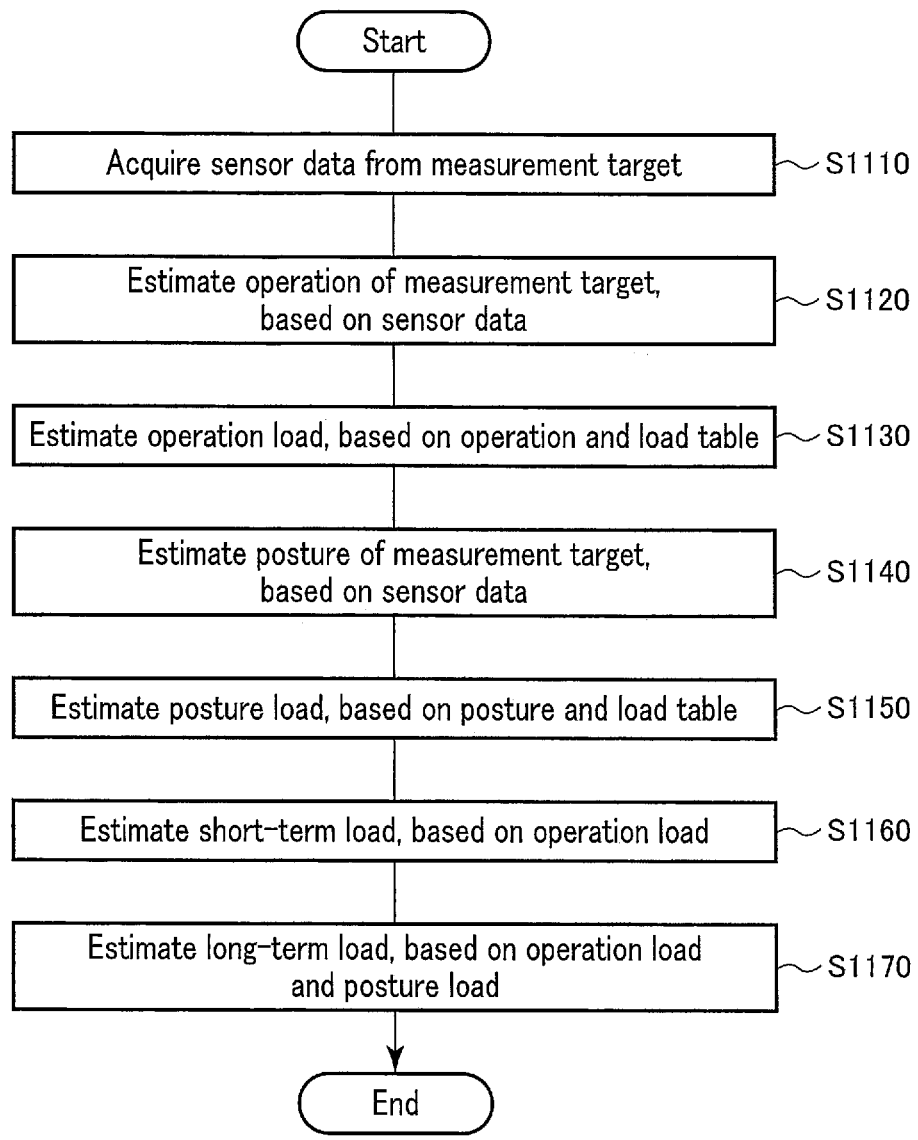
FIG. 11 is a flowchart illustrating an operation of the load estimation apparatus according to the second embodiment.

FIG. 11 is a flowchart illustrating the operation of the load estimation apparatus according to the second embodiment. The process of the flowchart of FIG. 11 starts when the load estimation program is executed by the user. Step S1110, step S1120, step S1140, step S1160 and step S1170 in the flowchart of FIG. 11 are respectively similar to step S410, step S420, step S440, step S460 and step S470 in the flowchart of FIG. 4. Therefore, a description thereof will be omitted.

(Step S1130)

After the operation is estimated in step S1120, the operation load estimation unit 530 estimates an operation load, based on the estimated operation and the load table.

(Step S1150)

After the posture is estimated in step S1140, the posture load estimation unit 550 estimates a posture load, based on the estimated posture and the load table.

As described above, the load estimation apparatus according to the second embodiment acquires sensor data from the measurement target, estimates an operation of a body part of the measurement target, based on the sensor data, estimates an operation load of the body part, based on operation information and the load table (first table), estimates a posture of the body part, based on the sensor data, estimates a posture load of the body part, based on posture information and the load table, estimates a first cumulative load, based on the operation load, and estimates a second cumulative load, which requires a longer load elimination time than the first cumulative load, based on the operation load and posture load.

Therefore, the load estimation apparatus according to the second embodiment can perform highly accurate load estimation for a short-term load and a long-term load by estimating the operation load and the posture load, using the load table.

Third Embodiment

In the connection with the first embodiment and the second embodiment, reference was made to the case where the operation load estimation and the posture load estimation are performed based on the operation and posture of a body part of a worker. On the other hand, in connection with the third embodiment, a description will be given of the case where the operation load estimation and the posture load estimation are performed in consideration of the work type as well.

FIG. 12 is a block diagram illustrating the configuration of the load estimation apparatus according to the third embodiment. The load estimation apparatus 1200 shown in FIG. 12 includes a data acquisition unit 1210, an operation estimation unit 1220, an operation load estimation unit 1230, a posture estimation unit 1240, a posture load estimation unit 1250, a short-term load estimation unit 1260 (first cumulative load estimation unit), a long-term load estimation unit 1270 (second cumulative load estimation unit), a model storage unit 1280 and a work type estimation unit 1290. The configurations of the operation estimation unit 1220, posture estimation unit 1240, short-term load estimation unit 1260 and long-term load estimation unit 1270 are similar to those of the operation estimation unit 220, posture estimation unit 240, short-term load estimation unit 260 and the long-term load estimation unit 270, and a description of the configurations will be omitted.

The data acquisition unit 1210 acquires sensor data from each of the first sensor 121, the second sensor 122, the third sensor 123 and the fourth sensor 124. The data acquisition unit 1210 outputs the acquired sensor data to the operation estimation unit 1220, the posture estimation unit 1240 and the work type estimation unit 1290.

The work type estimation unit 1290 receives the sensor data from the data acquisition unit 1210. The work type estimation unit 1290 estimates a work type of the measurement target, based on the sensor data. The work type estimation unit 1290 outputs information on the estimated work type (work type information) to the operation load estimation unit 1230 and the posture load estimation unit 1250.

Specifically, the work type estimation unit 1290 estimates the work type of the measurement target from the pattern of the sensor data. More specifically, the work type estimation unit 1290 estimates the work type, for example, by feature amount matching using a table in which a feature amount of the sensor pattern and a work type are associated with each other. The work type estimation unit 1290 may estimate the work type by executing one or more generally known algorithms. Further, the work type estimation unit 1290 may estimate the work type by using a learned machine learning model trained to output the work type in response to input of the sensor data.

The model storage unit 1280 stores a load table (first table) and a work type table (second table) in which work types and states of body parts are associated with each other. Work types are classified into, for example, trolley pushing, equipment assembly, brazing and heavy work. The model storage unit 1280 outputs a load table and a work type table to the operation load estimation unit 1230 and the posture load estimation unit 1250.

FIG. 13 is a table in which work types and states of a plurality of body parts are associated in the third embodiment. In the table 1300 (work type table) of FIG. 13, specific work types and states of body parts generated in the specific work types are associated with each other. For example, the work type "trolley pushing" is associated with the leg operation "walking", the leg posture "extension", the waist postures "extension" and "flexion", the forearm postures "keeping in air" and "relaxing" and the upper arm postures of "relaxing" and "keeping in air." For example, the waist operation, the forearm operation and the upper arm operation are not associated with the work type "trolley pushing." Thus, the operation loads that are not related to the work type are not estimated.

The operation load estimation unit 1230 receives operation information from the operation estimation unit 1220, receives work type information from the work type estimation unit 1290 and reads a load table and a work type table from the model storage unit 1280. The operation load estimation unit 1230 estimates an operation load, based on the operation information, the work type information, the load table and the work type table. The operation load estimation unit 1230 outputs information on the estimated operation load (operation load information) to the short-term load estimation unit 1260 and the long-term load estimation unit 1270.

Specifically, the operation load estimation unit 1230 determines the operation of the measurement target by using the work type information and the work type table. Where the operation information includes an operation of a body part and exercise intensity in the operation of the body part, the operation load estimation unit 1230 estimates a load value (operation load) by executing a predetermined operation (e.g., multiplication) using, for example, the coefficients corresponding to the exercise intensity in the operation of the body part and the operation of the body part. Where the operation of the body part included in the operation information and the operation to be calculated are different, the operation load estimation unit 1230 does not have to estimate a load value for the operation of the body part. Thus, the operations that are not related to the estimated work type can be excluded.

The posture load estimation unit 1250 receives posture information from the posture estimation unit 1240, receives work type information from the work type estimation unit 1290 and reads a load table and a work type table from the model storage unit 1280. The posture load estimation unit 1250 estimates a posture load, based on the posture information, the work type information, the load table and the work type table. The posture load estimation unit 1250 outputs information on the estimated posture load (posture load information) to the long-term load estimation unit 1270.

Specifically, the posture load estimation unit 1250 determines the posture of the measurement target by using the work type information and the work type table. Where the posture information includes a posture of a body part and duration of the posture of the body part, the posture load estimation unit 1250 estimates a load value (posture load) by executing a predetermined operation (e.g., multiplication) using, for example, the coefficients corresponding to the duration of the posture of the body part and the posture of the body part. Where the posture of the body part included in the posture information and the posture to be calculated are different, the posture load estimation unit 1250 does not have to estimate a load value for the posture of the body part. As a result, the postures that are not related to the estimated work type can be excluded.

The configuration of the load estimation apparatus 1200 according to the third embodiment has been described above. Next, the operation of the load estimation apparatus 1200 will be described with reference to the flowchart of FIG. 14.

FIG. 14 is a flowchart illustrating the operation of the load estimation apparatus according to the third embodiment. The process of the flowchart of FIG. 14 starts when the load estimation program is executed by the user. Step S1410, step S1430, step S1450, step S1470 and step S1480 in the flowchart of FIG. 14 are similar to step S410, step S420, step S440, step S460 and step S470 in the flowchart of FIG. 4. Therefore, a description thereof will be omitted.

(Step S1420)

After the sensor data is acquired in step S1410, the work type estimation unit 1290 estimates a work type of the measurement target, based on the sensor data.

(Step S1440)

After the operation is estimated in step S1430, the operation load estimation unit 1230 estimates an operation load, based on the estimated operation, the estimated work type, the load table and the work type table.

(Step S1460)

After the posture is estimated in step S1450, the posture load estimation unit 1250 estimates a posture load, based on the estimated posture, the estimated work type, the load table and the work type table.

As described above, the load estimation apparatus according to the third embodiment acquires sensor data from the measurement target, estimates a work type of the measurement target, based on the sensor data, estimates an operation of a body part of the measurement target, based on the sensor data, estimates an operation load of the body part, based on operation information, the work type information, the load table (first table), and the work type table (second table), estimates a posture of the body part, based on the sensor data, estimates a posture load of the body part, based on posture information, the work type information, the load table and the work type table, estimates a first cumulative load, based on the operation load, and estimates a second cumulative load, which requires a longer load elimination time than the first cumulative load, based on the operation load and posture load.

Therefore, the load estimation apparatus according to the third embodiment can perform highly accurate load estimation for a short-term load and a long-term load by estimating a work type and estimating an operation load and a posture load, using the load table and the work type table.

(Application Example of Third Embodiment)

In connection with the third embodiment, reference was made to the case where load estimation is performed by using the load table in which a state of the body part and a load coefficient are associated with each other and the work type table in which a work type and a state of a body part of the worker are associated with each other. In connection with the application example of the third embodiment, a description will be given of the case where load estimation is performed by using a table (work type load table) in which work types and load coefficients of body parts of the worker are associated with each other.

FIG. 15 is a table in which work types and the load coefficients of a plurality of body parts are associated in the application example of the third embodiment. In the table 1500 (work type load table) of FIG. 15, the work types are classified into four types: "trolley pushing", "equipment assembly", "brazing" and "heavy work." As an example, the work type "trolley pushing" is associated with a leg load coefficient "2", a waist load coefficient "1", a forearm load coefficient "2" and an upper arm load coefficient "3". The load coefficients of the work type load table are determined based on, for example, the average loads of the body parts according to the work types. The work type load table may be prepared for each of the operations of a body part and each of the postures of the body part.

FIG. 16 is a diagram illustrating how the exercise intensity of an upper arm and the state of the upper arm are related in the application example of the third embodiment. FIG. 16 shows a graph 1600 that expresses the exercise intensity of the upper arm in chronological order. For example, where the exercise intensity of the upper arm exceeds a first threshold value (threshold value th2), the operation estimation unit 1220 estimates that a load is generated (load generation) as a state of the upper arm.

Specifically, in the graph 1600, the exercise intensity of the upper arm increases from time t10, and at time t20, the exercise intensity of the upper arm exceeds the threshold value th2. In the graph 1600, the state in which the exercise intensity of the upper arm exceeds the threshold value th2 is maintained until the exercise intensity falls below the threshold value th2 at time t30, and the exercise intensity becomes the initial value (zero) at time t40.

The operation estimation unit 1220 estimates that a load is being generated from time t20 to time t30, and outputs operation information including information indicative of the load generation to the operation load estimation unit 1230. The operation load estimation unit 1230 estimates an operation load, based on the operation information, the work type information and the work load table. For example, the operation load estimation unit 1230 reads a load coefficient of the body part, using the work type information and the work load table, and during the period of the load generation, estimates a load value (operation load) by performing a predetermined calculation (e.g., multiplication), using the exercise intensity in the operation of the body part and the load coefficient of the body part.

As can be seen from the above, the load estimation apparatus according to the application example of the third embodiment can estimate a load value according to a work type even if a detailed state of a body part is not estimated. Thus, the operation estimation unit and the posture estimation unit do not have to perform highly accurate estimation, so that the running cost of the load estimation apparatus can be expected to be reduced.

FIG. 17 is a table in which a measurement target and long-term cumulative load values of a plurality of body parts are associated in one embodiment. Table 1700 in FIG. 17 is a list of cumulative load values (long-term cumulative load values) resulting from long-term loads for each measurement target, and is displayed on the output device 110 as display data, for example. In the table 1700, for example, worker A and worker B are displayed in the column of the measurement target. In the row of the worker A, "40" is displayed as the long-term cumulative load value of the leg, "20" is displayed as the long-term cumulative load value of the waist", "10" is displayed as the long-term cumulative load value of the forearm, and "10" is displayed as the long-term cumulative load value of the upper arm. In the row of the worker A, the long-term cumulative load value "40" of the leg is displayed with emphasis (e.g., with hatching). This means that this long-term cumulative load value exceeds a predetermined threshold value (e.g., 40 or more). The predetermined threshold value mentioned here is, for example, the work quota for the day.

In the row of the worker B, "20" is displayed as the long-term cumulative load value of the leg, "40" is displayed as the long-term cumulative load value of the waist, "50" is displayed as the long-term cumulative load value of the forearm, and "30" is displayed as the long-term cumulative load value of the upper arm. In the row of the worker B, the long-term cumulative load value "40" of the leg and the long-term cumulative load value "50" of the forearm are displayed with emphasis.

As described above, the load estimation apparatus according to one embodiment can visualize the long-term loads of the body parts of measurement targets. Thus, the administrator who uses the load estimation system can allocate appropriate work and a break to a measurement target by checking the long-term cumulative load values of the measurement target displayed on the output device 110.

FIG. 18 is a block diagram illustrating a hardware configuration of a computer according to one embodiment. The computer 1800 includes a CPU (Central Processing Unit) 1810, a RAM (Random Access Memory) 1820, a program memory 1830, an auxiliary storage device 1840 and an input/output interface 1850. These elements are provided as hardware. The CPU 1810 communicates with the RAM 1820, the program memory 1830, the auxiliary storage device 1840 and the input/output interface 1850 via a bus 1860.

The CPU 1810 is an example of a general-purpose processor. The RAM 1820 is used as a working memory by the CPU 1810. The RAM 1820 includes a volatile memory such as an SDRAM (Synchronous Dynamic Random Access Memory). The program memory 1830 stores various programs including a load estimation program. As the program memory 1830, for example, a ROM (Read-Only Memory), a portion of the auxiliary storage device 1840, or a combination of these is used. The auxiliary storage device 1840 stores data non-temporarily. The auxiliary storage device 1840 includes a nonvolatile memory such as an HDD or an SSD.

The input/output interface 1850 is an interface for coupling to or communicating with another device. The input/output interface 1850 is used, for example, for coupling to or communicating with the output device 110, first sensor 121, second sensor 122, third sensor 123 and fourth sensor 124 shown in FIG. 1.

Each of the programs stored in the program memory 1830 includes computer executable instructions. When the program (computer executable instructions) is executed by the CPU 1810, it causes the CPU 1810 to execute a predetermined process. For example, when the load estimation program is executed by the CPU 1810, it causes the CPU 1810 to execute a series of processes described in relation to the elements shown in FIGS. 2, 5 and 12.

The program may be provided to the computer 1800 in a state of being stored in a computer-readable storage medium. In this case, for example, the computer 1800 further includes a drive (not shown) that reads data from the storage medium, and acquires the program from the storage medium. Examples of storage media include a magnetic disk, optical disks (CD-ROM, CD-R, DVD-ROM, DVD-R, etc.), magneto-optical disks (MO, etc.) and a semiconductor memory. Alternatively, the program may be stored in a server on a communication network such that the computer 1800 can download the program from the server using the input/output interface 1850.

The processes described in connection with the embodiments are not limited to those which the general-purpose hardware processor, such as the CPU 1810, executes according to a program, and may be performed by a dedicated hardware processor such as an ASIC (Application Specific Integrated Circuit). The term processing circuit (processing unit) includes at least one general-purpose hardware processor, at least one dedicated hardware processor, or a combination of at least one general-purpose hardware processor and at least one dedicated hardware processor. In the example shown in FIG. 18, the CPU 1810, the RAM 1820 and the program memory 1830 correspond to the processing circuit.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A load estimation apparatus comprising:
    processing circuitry configured to
        acquire sensor data from a measurement target,
        estimate an operation of a body part of the measurement target, based on the sensor data,
        estimate an operation load of the body part, based on the estimated operation of the body part,
        estimate a posture of the body part, based on the sensor data,
        estimate a posture load of the body part, based on the estimated posture of the body part,
        estimate a first cumulative load, based on the estimated operation load, and
        estimate a second cumulative load based on the estimated posture load until the first cumulative load exceeds a threshold, and based on the estimated operation load and the estimated posture load after the first cumulative load exceeds the threshold, wherein the second cumulative load is different from the first cumulative load by the nature of a load; and
    a display configured to display data based on the estimated first cumulative load and the estimated second cumulative load.

2. The apparatus according to claim 1, wherein the processing circuitry is further configured to estimate the second cumulative load, based on a number of times an identical operation load is performed in a predetermined time and duration of the posture load.

3. The apparatus according to claim 1, wherein the processing circuitry is further configured to decrease a cumulative load addition rate in accordance with an increase in a number of times an identical operation load is performed in a predetermined time.

4. The apparatus according to claim 1, wherein the processing circuitry is further configured to calculate a prediction time for load elimination, based on the second cumulative load.

5. The apparatus according to claim 1, further comprising:
    a memory that stores a first table in which the operation and the posture are associated with a load coefficient, wherein
    the estimated operation load is estimated based on the estimated operation of the body part and the first table, and
    the estimated posture load is estimated based on the estimated posture of the body part and the first table.

6. The apparatus according to claim 5, wherein the load coefficient is based on at least one of a ratio of a weight of the body part to a weight of a whole body or a relationship between the weight of the body part and muscle mass of the body part.

7. The apparatus according to claim 6, wherein
    the processing circuitry is further configured to estimate a type of work performed by the measurement target, based on the sensor data,
    the memory stores a second table in which the type of work is associated with the operation and the posture, and
    the processing circuitry is further configured to
        estimate the operation load, based on the estimated operation of the body part, the first table, the type of work and the second table, and
        estimate the posture load, based on the estimated posture of the body part, the first table, the type of work and the second table.

8. The apparatus according to claim 1, wherein the first cumulative load is a load eliminated by taking a rest for a period less than a predetermined period of time and the second cumulative load is a load eliminated by taking a rest for a period more than the predetermined period of time.

9. The apparatus according to claim 1, wherein the nature of the load is determined based on whether the load is eliminated by taking a rest for a period less than or more than a predetermined period of time.

10. A load estimation method comprising:
    acquiring sensor data from a measurement target;
    estimating an operation of a body part of the measurement target, based on the sensor data;
    estimating an operation load of the body part, based on the estimated operation of the body part;
    estimating a posture of the body part, based on the sensor data;
    estimating a posture load of the body part, based on the estimated posture of the body part;
    estimating a first cumulative load, based on the estimated operation load;
    estimating a second cumulative load based on the estimated posture load until the first cumulative load exceeds a threshold, and based on the estimated operation load and the estimated posture load after the first cumulative load exceeds the threshold, wherein the second cumulative load is different from the first cumulative load by the nature of a load; and
    displaying data based on the estimated first cumulative load and the estimated second cumulative load.

11. A non-transitory computer-readable storage medium storing a program for causing a computer to execute processing comprising:
    acquiring sensor data from a measurement target;

estimating an operation of a body part of the measurement target, based on the sensor data;
estimating an operation load of the body part, based on the estimated operation of the body part;
estimating a posture of the body part, based on the sensor data;
estimating a posture load of the body part, based on the estimated posture of the body part;
estimating a first cumulative load, based on the estimated operation load;
estimating a second cumulative load based on the estimated posture load until the first cumulative load exceeds a threshold, and based on the estimated operation load and the estimated posture load after the first cumulative load exceeds the threshold, wherein the second cumulative load is different from the first cumulative load by the nature of a load; and
displaying data based on the estimated first cumulative load and the estimated second cumulative load.

* * * * *